US010595523B2

(12) United States Patent
Martens et al.

(10) Patent No.: US 10,595,523 B2
(45) Date of Patent: Mar. 24, 2020

(54) FORCED AIR PESTICIDE VAPORIZER WITH HEATSINK VAPORIZATION CHAMBER AND OFFSET EXHAUST CHAMBER

(71) Applicant: Techtoba Inc., Grunthal (CA)

(72) Inventors: Allen John Martens, Grunthal (CA); Kristopher Bryan Martens, Winnipeg (CA)

(73) Assignee: Techtoba Inc., Grunthal (CA)

( * ) Notice: Subject to any disclaimer, the term of this patent is extended or adjusted under 35 U.S.C. 154(b) by 270 days.

(21) Appl. No.: 15/809,390

(22) Filed: Nov. 10, 2017

(65) Prior Publication Data

US 2019/0141980 A1 May 16, 2019

(51) Int. Cl.

*A01K 51/00* (2006.01)
*A01M 1/20* (2006.01)
*A01N 37/04* (2006.01)
*A01K 55/00* (2006.01)

(52) U.S. Cl.

CPC ........... *A01M 1/2061* (2013.01); *A01K 51/00* (2013.01); *A01K 55/00* (2013.01); *A01M 1/2077* (2013.01); *A01N 37/04* (2013.01)

(58) Field of Classification Search

CPC ........ A01N 37/04; A01N 25/18; A01N 25/20; A01K 51/00; A01K 55/00; A01M 1/2061; A01M 1/2077

USPC .......................................................... 43/129

See application file for complete search history.

(56) References Cited

U.S. PATENT DOCUMENTS 2,690,500 A * 9/1954 Winberg ............. A01M 1/2077 392/392
4,871,115 A * 10/1989 Hessey ................... A63J 5/025 239/136
2004/0121039 A1* 6/2004 Olaru ................. B29C 45/2737 425/549
2012/0104119 A1* 5/2012 Benalikhoudja ...... B05B 7/0012 239/398
2014/0048620 A1* 2/2014 Semenov .............. B05B 7/1686 239/136
2016/0370151 A1* 12/2016 Batts ......................... F41H 9/06

(Continued)

FOREIGN PATENT DOCUMENTS

DE 202004005675 U1 * 9/2004 .......... A01M 1/2088

*Primary Examiner* — Claude J Brown

(74) *Attorney, Agent, or Firm* — Kyle R Satterthwaite; Ryan W Depuis; Ade & Company Inc

(57) ABSTRACT

An apparatus for vaporizing and dispensing a pesticide features an elongated body structure, and heatsink attached to the elongated body structure at a distal end thereof. A loading port on the elongated structure feeds solid pesticide material into a closed-ended vaporization chamber inside the heatsink via a delivery passage running longitudinally of the elongated structure. A heater is operably arranged with the heatsink to vaporize the solid pesticide material. The heatsink interior features a second exhaust chamber that is radially offset from the vaporization chamber, and is only fluidly communicated therewith by a radial port near the end of the vaporization chamber fed by the delivery passage. The loaded solid pesticide falls past the radial port into the vaporization chamber, while the resulting vapor is forced through the radial port into the exhaust chamber by pressurized air fed through the delivery passage.

21 Claims, 5 Drawing Sheets

(56) References Cited

U.S. PATENT DOCUMENTS

2017/0188550 A1* 7/2017 Maher .................... A01K 51/00
2017/0367407 A1* 12/2017 Althorpe ............... A24F 47/008
2018/0263222 A1* 9/2018 Oster .................... A01K 51/00
2018/0317458 A1* 11/2018 Puzankov ........... A01M 1/2072

* cited by examiner

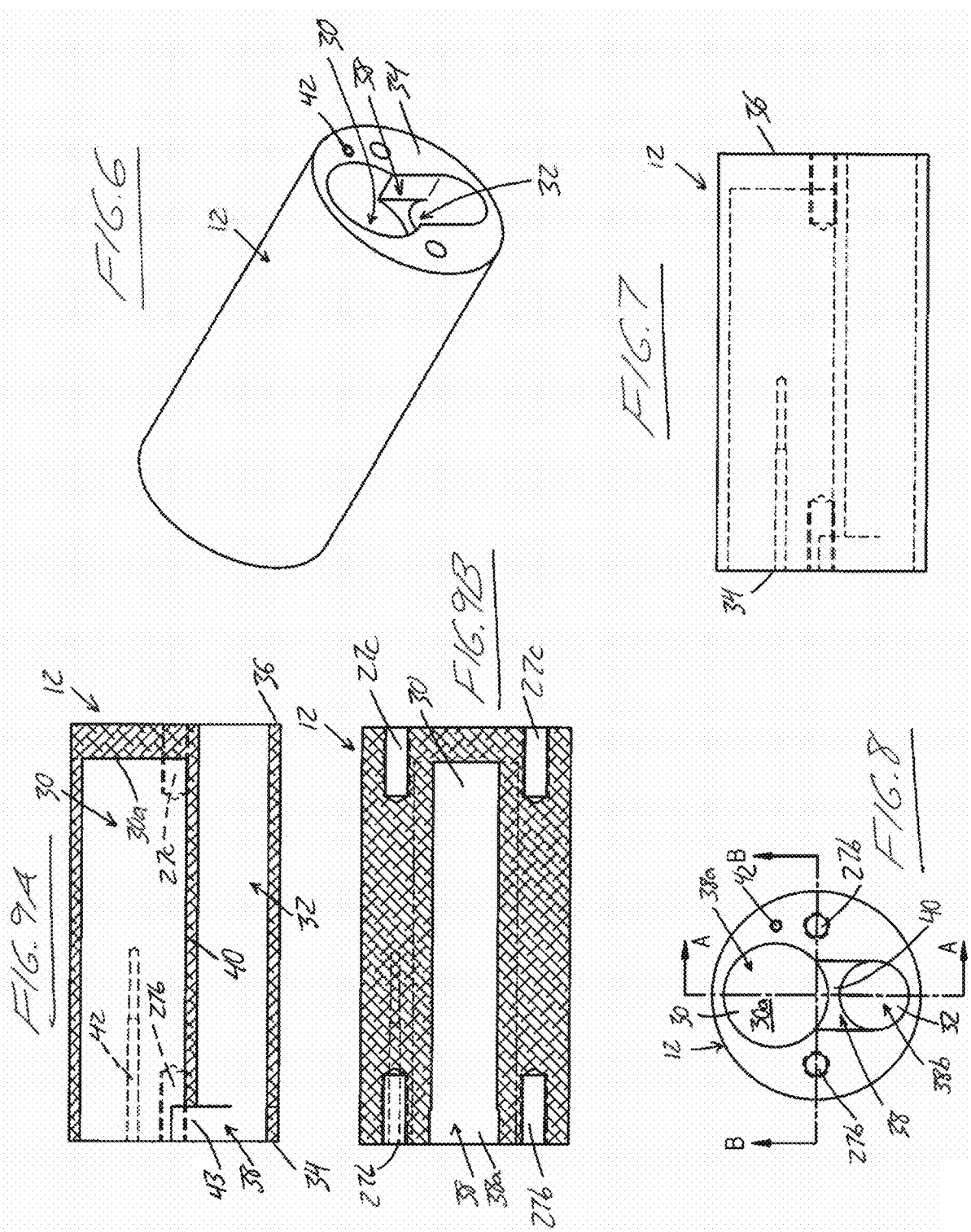

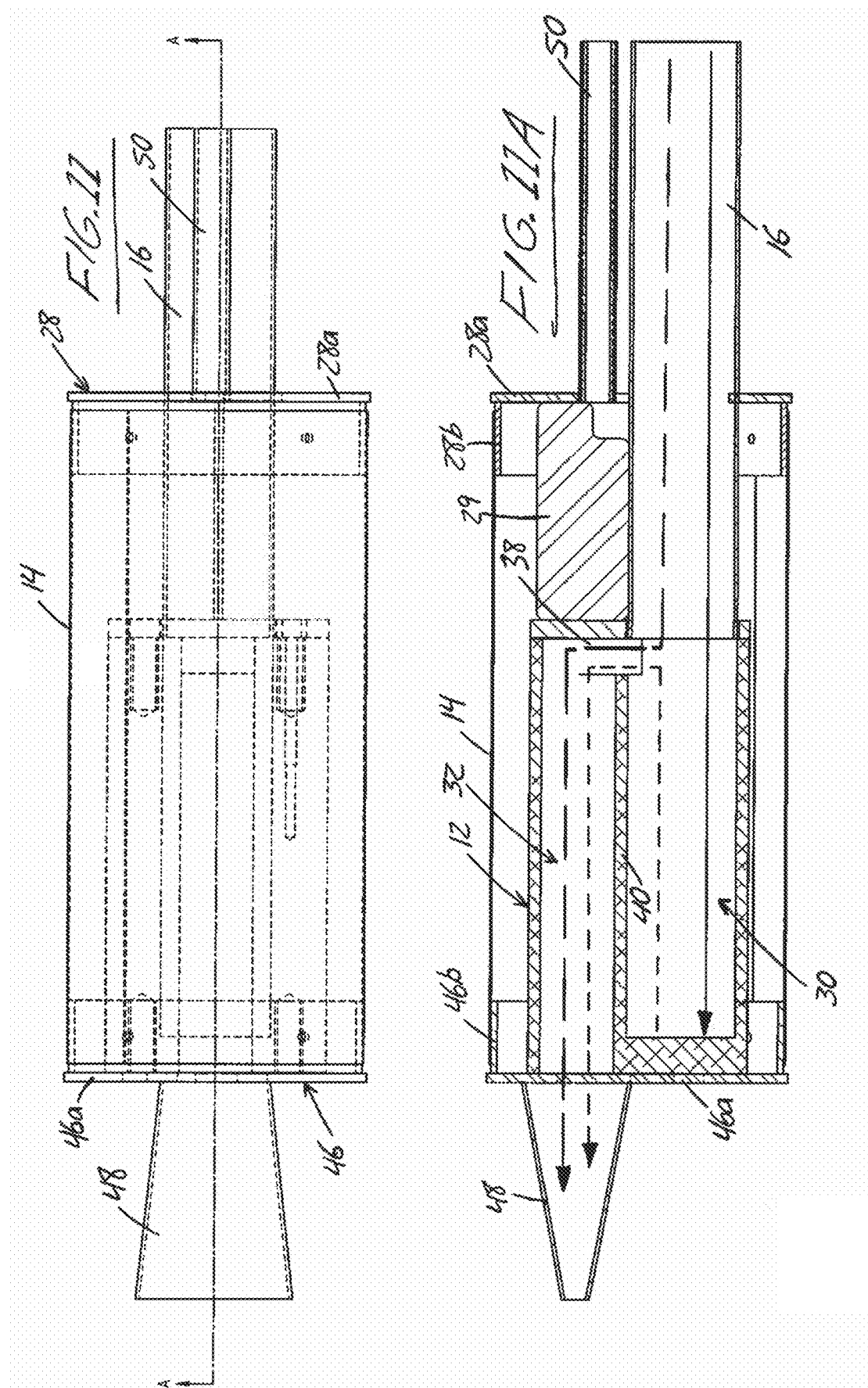

FORCED AIR PESTICIDE VAPORIZER WITH HEATSINK VAPORIZATION CHAMBER AND OFFSET EXHAUST CHAMBER

FIELD OF THE INVENTION

The present invention relates generally to beekeeping tools and vaporizing devices, and more particularly to forced air pesticide vaporizers to deliver vaporized oxalic acid to bee hives for the purpose of exterminating varroa mites.

BACKGROUND

Vaporizers operable to perform sublimation of oxalic acid crystals and application of the resulting vapour to beehives for the extermination of varroa mites are known. Some of the known devices included forced-air units for blowing the generated vapor into the hive.

For example, U.S. Pat. No. 7,578,722 discloses a forced air vaporization and dispensing apparatus using a fan to help dispense the vaporized oxalic acid into a bee hive.

U.S. Pat. No. 9,655,346 instead relies on connection of a separate air compressor to a wand-like vaporization and dispensing tool. The oxalic acid is loaded into a primary tube of the tool at a proximal end thereof, and vaporized in the same tube by a heater coil wrapped around the opposing distal end of the tube. Pressurized air is introduced to the tube by a pair of nozzles at an intermediate location along the tube so that this forced air will blow the resulting oxalic acid vapor through a diffuser at the distal end. A screen near the distal end of the tube captures the crystals to prevent them from escaping the tube before they are vaporized.

However, there remains room for improvement, and Applicant has developed a new pesticide vaporization and dispensing tool with a unique combination of features not shown or suggested by the prior art.

SUMMARY OF THE INVENTION

According to one aspect of the invention, there is provided an apparatus for vaporizing and dispensing a pesticide agent, said apparatus comprising:

an elongated body structure having a proximal end, an opposing distal end and a delivery passage running longitudinally of the elongated body structure to the distal end thereof;

a heatsink of thermally conductive material attached to said elongated body structure at the distal end thereof and comprising a hollow interior into which the delivery passage of the elongated body structure opens at the distal end thereof;

a loading port on the elongated body structure at or proximate the proximal end thereof for introduction of solid pesticide material into the delivery passage for delivery onward therethrough to the hollow interior of the heatsink;

a heater operably arranged with the heatsink to vaporize the solid pesticide material received in the hollow interior of the heatsink through the elongated body structure; and a vapour outlet fluidly communicating the hollow interior of the heatsink to an exterior environment to exhaust the vaporized pesticide from the apparatus to a targeted treatment area.

Preferably the heatsink exceeds the elongated body structure in wall thickness.

Preferably the heatsink comprises a bored-out solid body of said thermally conductive material.

Preferably the thermally conductive material of the heatsink is aluminum.

Preferably the thermally conductive material of the heatsink has greater thermal conductivity than a constituent material of the elongated body structure.

Preferably the proximal and distal ends of the elongated body structure are separated in an axial direction, the hollow interior of the heatsink comprises a vaporization chamber and an exhaust chamber, the vaporization chamber has a first open end into which the delivery passage opens and a closed second end axially opposite the first open end, and the exhaust chamber is radially offset from the vaporization chamber and is fluidly communicated therewith near the first end thereof.

Preferably the exhaust chamber communicates with the vaporization chamber and the vapor outlet adjacent axially opposing ends of said exhaust chamber.

Preferably the chambers are in fluid communication with one another only at areas thereof adjacent the distal end of the elongated body structure.

Preferably the chambers comprise respective cylindrical bores.

Preferably the respective cylindrical bores of the chambers are fluidly communicated with one another at a counter-bored end of the heatsink.

Preferably the heater is disposed circumferentially around both the vaporization chamber and the exhaust chamber.

Preferably the heater is a band heater defining a cylindrical shell around the heatsink.

Preferably there is a temperature sensor operably installed on the heatsink to monitor temperature conditions thereof and connected to a controller arranged to automatically control the heater in response to detected changes in said temperatures conditions.

According to another aspect of the invention, there is provided an apparatus for vaporizing and dispensing a pesticide agent, said apparatus comprising:

an elongated body structure having a proximal end, an opposing distal end spaced therefrom in an axial direction and a delivery passage running longitudinally of the elongated body structure to the distal end thereof;

a vaporization chamber carried at the distal end of the elongated body structure, where the delivery passage of the elongated body structure opens into said vaporization chamber;

a loading port on the elongated body structure at or proximate the proximal end thereof for introduction of solid pesticide material into the delivery passage for delivery onward therethrough to the vaporization chamber;

a heater operably arranged with the vaporization chamber to vaporize the solid pesticide material received therein through the delivery passage to generate a pesticidal vapour; and an exhaust chamber for receiving the pesticidal vapour from the vaporization chamber; and a vapour outlet fed by the exhaust chamber to exhaust the pesticidal vapour from the apparatus to a targeted treatment area;

wherein the vaporization chamber has a first open end into which the delivery passage opens and a closed second end axially opposite the first open end, and the exhaust chamber is radially offset from the vaporization chamber and is fluidly communicated therewith near the first end thereof.

Preferably the exhaust chamber communicates with the vaporization chamber and the vapor outlet adjacent axially opposing ends of said exhaust chamber.

Preferably the chambers are in fluid communication with one another only at areas thereof adjacent the distal end of the elongated body structure.

Preferably the chambers comprise respective cylindrical bores in a shared body of material.

Preferably the respective cylindrical bores of the chambers are fluidly communicated with one another at a counter-bored end of the shared body of material.

Preferably there is a forced air system for pressurized conveyance of the pesticidal vapour from the vaporization chamber to the vapour outlet via the exhaust chamber, said forced air system comprising a nozzle arranged to introduce a supply of pressurized air into the delivery passage and direct said supply of pressurized air through said delivery passage to the vaporization chamber.

Preferably said nozzle is an only nozzle of said forced air system, which further comprises two different supply branches that both feed said only nozzle, one of said branches comprising a burst control valve operable from a normally closed state to an open state to momentarily open said one said branches to augment a steady supply of air through the other branch with a momentary burst of additional air.

BRIEF DESCRIPTION OF THE DRAWINGS

One embodiment of the invention will now be described in conjunction with the accompanying drawings in which:

FIG. 6 is a perspective view of a heatsink chamber body of the apparatus of FIG. 1.

FIG. 7 is a side elevational view of the heatsink chamber body of FIG. 6.

FIG. 8 is an end elevational view of the heatsink chamber body of FIG. 6.

FIGS. 9A and 9B are cross-sectional views of the heatsink chamber body as viewed along lines A-A and B-B thereof, respectively.

FIG. 11 is an enlarged partial top plan view of the apparatus of FIG. 1.

FIG. 11A is a partial cross-sectional view of the apparatus of FIG. 11 as viewed along line A-A thereof, and includes schematically illustrated travel paths followed by solid pesticide material, resulting vapor and pressurized air from the forced air system of FIG. 10 during use of the apparatus.

DETAILED DESCRIPTION

Figure 1:
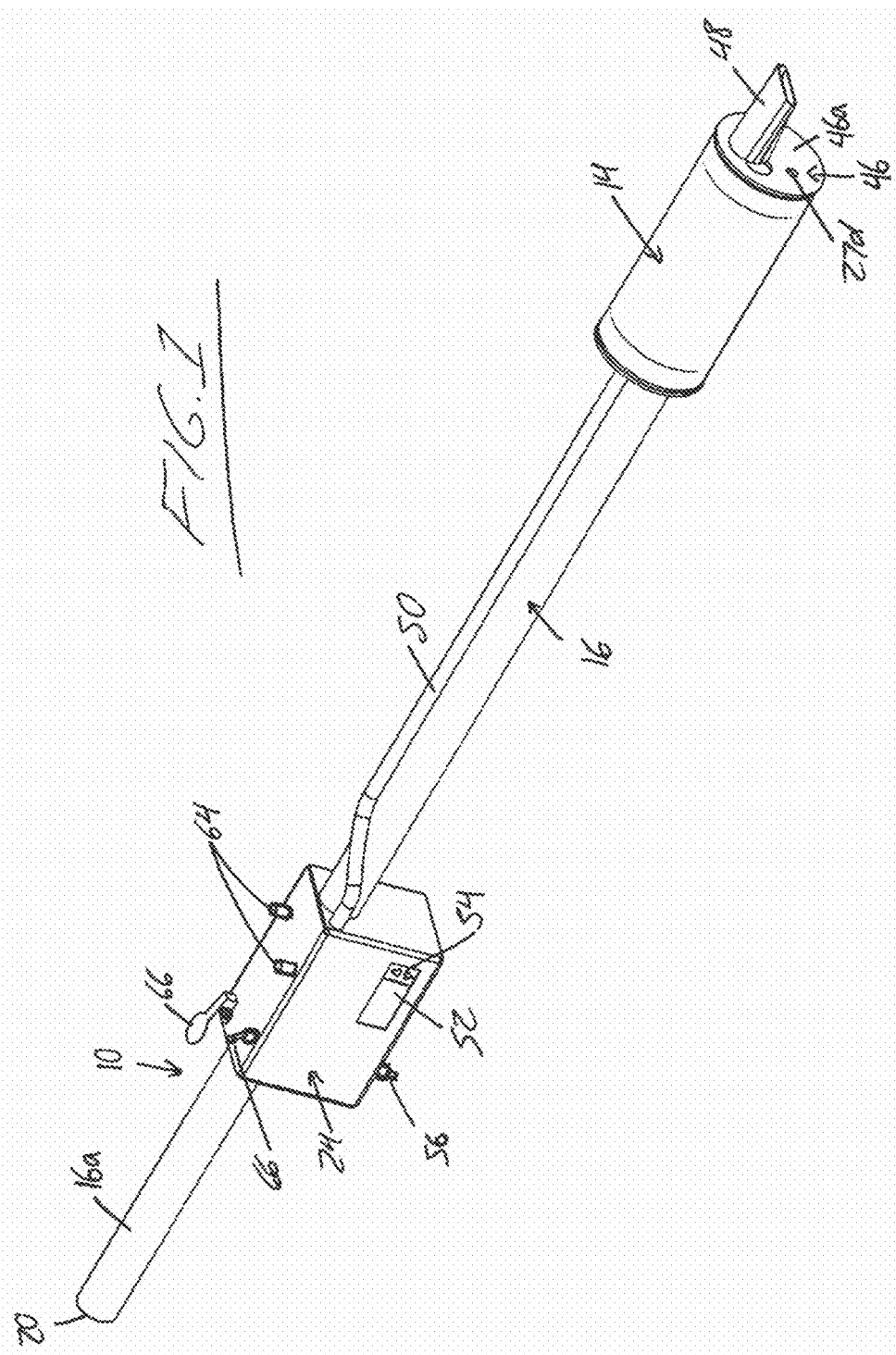
FIG. 1 is a perspective view of a pesticide vaporizing and dispensing apparatus of the present invention.
Figure 2:
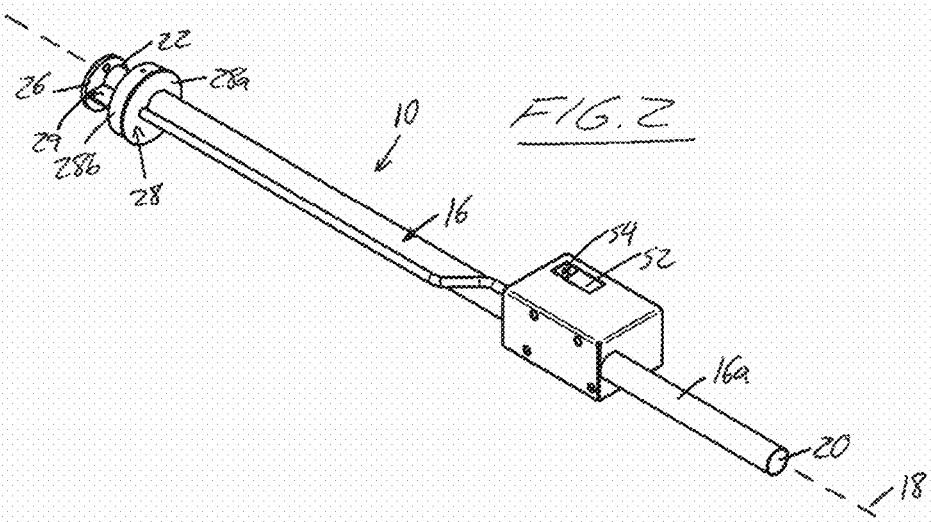
FIG. 2 is a perspective view of an elongated main body structure of the apparatus of FIG. 1.
Figure 3:
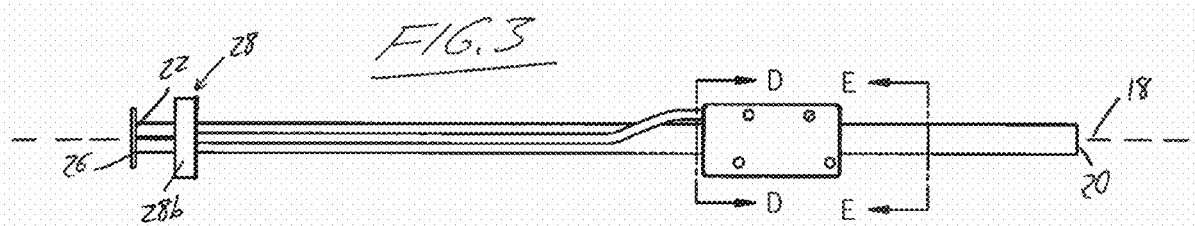
FIG. 3 is a top plan view of the main body structure of FIG. 2.
Figure 4:
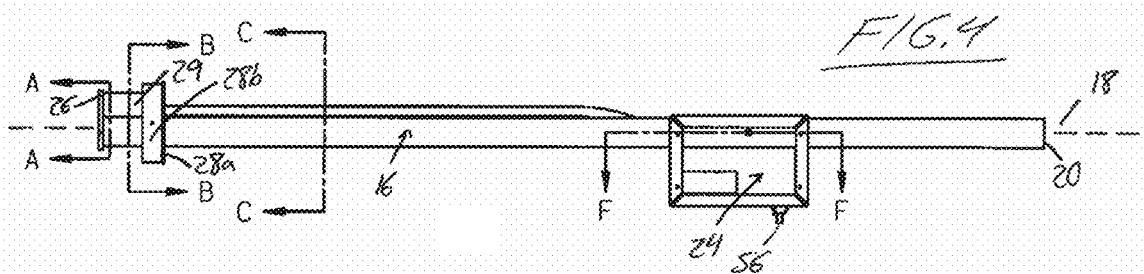
FIG. 4 is a side elevational view of the main body structure of FIG. 3.

FIG. 1 illustrates an apparatus of the present invention designed for vaporization of oxalic acid crystals and forced-air dispensing of the resulting oxalic acid vapor into a beehive in order to exterminate varroa mites. Though framed herein with this particular purpose in mind, it will be appreciated that the apparatus may be similarly employed for the vaporization and forced air dispensing of other initially solid pesticide agents in a vaporized state.

The fully assembled apparatus is made up of a elongated wand-like main body structure 10, a heatsink chamber body 12 affixed to an end of the main body structure 10, and a band heater 14 affixed to the main body structure near the same end thereof so as to enclose around the heatsink chamber body in manner operable to elevate the heatsink temperature to a suitable range to vaporize the oxalic crystals loaded into the apparatus.

Referring to FIGS. 2 through 5, the main body structure 10 features a primary tube 16 in the form of a rigid length of pipe extending linearly on a central longitudinal axis 18 from a proximal end 20 of the main body structure to an axially opposing distal end 22. The primary tube 16 is hollow throughout, and open at both the proximal and distal ends. The open proximal end 20 of the tube 16 serves as a loading port through which oxalic acid crystals are loaded into the apparatus in their original solid state for subsequent vaporization of these crystals inside the apparatus.

A control unit housing 24 is affixed to the primary tube 16 at an intermediate location between the proximal and distal ends thereof, more particularly at a location nearer to, but spaced from, the proximal end 20. The proximal portion 16a of the tube 16 left exposed between the control unit housing 24 and the proximal end of the tube 16 defines a hand grip area for manual support of the apparatus in a wand-like fashion. At the opposing distal end 22 of the primary tube 16, a heatsink mounting flange 26 is defined by a round annular plate that projects radially outward from around the open distal end 22 of the primary tube 16. The heatsink mounting flange 26 features bolt holes 27a therein on opposite sides of the primary tube 16 for bolted fastening of the heatsink chamber body 12 to the distal end of the main body structure. The heatsink mounting flange 26 is non-concentric with the primary tube 16, as perhaps best shown in FIG. 5A, where the central longitudinal axis 18 of the primary tube 16 clearly does not coincide with the center of the circular mounting flange 26. The primary tube 16 is thus offset from the center of the flange 26 to reside nearer to one side of the flange's circular outer periphery than to a diametrically opposite side thereof.

Spaced a short axial distance along the primary tube 16 from the heatsink mounting flange 26 is a heater mount 28 that likewise features a round annular plate 28a projecting radially outward from the primary tube 16 in non-concentric relation thereto. The centers of the heatsink mounting flange 26 and the heater mount share are aligned with one another on a shared central axis that is radially offset from, but parallel to, the central longitudinal axis 18 of the primary tube 16. The heater mount 28 also features a short cylindrical collar 28b mounted concentrically on the annular plate 28a near the outer circumference thereof. The collar 28b reaches toward the heatsink mounting flange 26. In the fully assembled state of the apparatus, one end of the cylindrical band heater 14 fits externally over the collar 28b to support the band heater 14 on the main body structure 10.

As shown in the drawings, a stiffening fin 29 is affixed to the primary tube 16 at the portion thereof between the heatsink mounting flange 26 and the heater mount 29. The stiffening fin projects radially from the primary tube 26 to the same side thereof to which the heatsink mounting flange 26 is offset from the longitudinal axis 18 of the primary tube. The fin 29 reaches the distal end of the tube 16, where the fin is affixed to the heatsink mounting flange 26, and serves as a stiffening gusset between the primary tube 16 and the heatsink mounting flange 26 to help support the weight of the heatsink by resisting deflection between the tube and the mounting flange 26.

FIG. 6 illustrates the heatsink chamber body 12, which is a unitary solid body of heat conductive material such as brass or aluminum. While a brass heatsink is known to be more thermally conductive than aluminum, thus forming a more effective heatsink, aluminum is often more preferable in the interest of a more cost-effective construction. The heatsink chamber body 12 of the illustrated embodiment has a cylindrical outer shape, though the external shape may vary in other embodiments. The heatsink chamber body 12 has an axial length that is measured parallel to the central longitudinal axis 18 of the primary tube 16 and the shared central axis of the heatsink and heater mounts 26, 28. This axial length of the heatsink chamber body exceeds its width or diameter, which is measured orthogonally of axial length in planes normal thereto.

The heatsink chamber body 12 has two axial bores machined therein, each defining a respective cylindrical chamber within the heatsink chamber body 12. A larger-diameter one of these two axial bores defines a vaporization chamber 30 for receiving the oxalic acid crystals loaded into the apparatus, and holding these crystals during sublimation thereof into a vaporized state. The smaller-diameter bore defines an exhaust chamber 32 through which the vaporized oxalic acid is subsequently exhausted from the vaporization chamber 30.

The exhaust chamber 32 is a through-bore that fully spans the axial length of the heatsink chamber body 12 from one end thereof to the other. On the other hand, the vaporization chamber 30 is a blind-bore that opens into the heatsink chamber body only at the attachment end 34 thereof that is affixed to the heatsink mounting flange 26 in the assembled state of the apparatus. The vaporization chamber 30 stops short of the axially opposing discharge end 36 of the heatsink chamber body 12. The vaporization chamber thus has a closed end wall 30a preventing solid oxalic acid crystals or vaporized oxalic acid from axially exiting the vaporization chamber through the discharge end 36 of the heatsink chamber body 12. Both chambers 30, 32 are therefore open at the attachment end 34 of the heatsink body 12, while only the exhaust chamber 32 is open at the discharge end 36 of the heatsink body. The attachment end 34 of the heatsink chamber body 12 has an enlarged counterbore 38 recessed axially therein and at least partially overlapping both the vaporization chamber 30 and the exhaust chamber 32. Accordingly, the two chambers 30, 32 are fluidly communicated with one another in a radial direction at this counterbored area 38. Over the entire axial remainder of the of the vaporization chamber 30 reaching from the counterbored area 38 to the closed end 30a of the vaporization chamber, the two chambers 30, 32 are physically isolated from one another by a solid divider wall portion 40 of the heatsink body that remains intact between the two chambers 30, 32.

Neither of the two chambers is concentric with the outer cylindrical shape of the heatsink chamber body 12, each instead being nearer to a respective one of two diametrically opposing sides thereof. In the fully assembled state of the apparatus, the cylindrical shape of the heatsink chamber body is centered on the shared central axis of the heatsink and heater mounts 26, 28, while the cylindrical shape of the vaporization chamber 30 is centered on the central longitudinal axis 18 of the primary tube 16.

The counterbore 38 of the illustrated embodiment has a keyslot shape, with an enlarged circular upper lobe 38a that is centered on the same axis as the vaporization chamber and is of similar diameter thereto, and a U-shaped bottom stem 38b that juts radially from the circular lobe and has a narrower width of similar measure to the diameter of the smaller-bore exhaust chamber 32. The curved outer end of the U-shaped stem 38b generally conforms with the semi-cylindrical bottom half of the exhaust chamber 32 that lies furthest from the vaporization chamber 30.

The attachment end 34 of the heatsink cavity body 12 also features a pair of bolt holes 27b on opposite sides of the counterbore 38. These bolt holes 27b are sized and positioned to align with the bolt holes 27a on the heatsink mounting flange 26. The heatsink cavity body 12 is thus bolted to the heatsink mounting flange 26, and the hollow interior of the primary tube 16 opens into the larger circular lobe 38a of the counterbore 38, which is of equal or similar diameter to the primary tube 16. The primary tube 16 stops short of, or only partially reaches into, the counterbore 38 so as not to obstruct fluid communication between the two chambers 30, 32 of the heatsink via the counterbore 38. That is, the counterbore leaves a gap 43 between the divider wall portion 40 of the heatsink body 12 and the face of the heatsink mounting flange 26, which abuts against the attachment end 34 of the heatsink chamber body 12. This gap 43 thus serves as a radial port between the two chambers by which vapor from the vaporization chamber can flow into the exhaust chamber, as described in more detail further below.

In addition to the blind bolt holes 27b, the attachment end 34 of the heatsink cavity body 12 also features an additional blind mounting hole 42 therein at a radial distance outward from the counterbore 38 to accommodate mounting of a thermocouple or other temperature sensor within the solid heatsink chamber body 12 at a location near but outside the vaporization chamber 30. The opposing discharge end 36 of the heatsink chamber body 12 features another set of blind bolt holes 27c therein.

Turning back to FIG. 1, the cylindrical band heater 14 has one end slipped over and fastened to the collar 28b of the heater mount 28. The band heater 14 has an axial length generally equal to the distance from the flange 28a of the heater mount 28 to the discharge end 36 of the heatsink cavity body 12. Here, an end cap 46 of similar structure to the heater mount 28 has a circular end plate 46a overlying the discharge end 36 of the heatsink cavity body, and a cylindrical collar 46b jutting a short axial distance back toward the matching collar 28b of the heater mount 28. This collar 46b circumferentially receives the second end of the band heater 14, and is fastened thereto. The cylindrical band heater 14 thus circumferentially surrounds the heatsink chamber body 12 over the full axial length thereof. A diffuser 48 is attached to the end plate 46a of the end cap 46 to serve as the final outlet of the vaporized oxalic acid from the apparatus. The diffuser or other output is fluidly communicated with the open discharge end of the exhaust chamber 32 of the heatsink chamber body 12 via one or more holes in the end plate 46a. The end plate features a pair of bolt holes 27d passing therethrough, one of which is visible in FIG. 1. These bolt holes 27d that align with the bolt holes 27c in the discharge end 36 of the heatsink chamber body 12 for fastening of the end cap 46 thereto.

A communications cable 50 runs from the control unit housing 24 to the heater mount 28, and carries internal wiring (not shown) that connects up with the band heater 14 and the temperature sensor in the mounting hole 42 of the heatsink chamber body 12 in order to control operation of the heater 14. A temperature control module in the control unit housing 24 is responsible for such heater control, and shown may include an indicator 52 viewable at the exterior of the control unit housing 24 so that an operator can be sure a sufficient operating temperature is present in the heatsink to achieve sublimation of the oxalic acid in the vaporization chamber. In the illustrated embodiment, the control indicator 52 is a temperature readout screen operable to show the actual temperature detected by the temperature sensor, though in other embodiments, a more simplistic display simply switching between "ready" and "unready" indicators may be employed (e.g. using differently coloured indicator lamps, such as light emitting diodes (LEDs)). Pushbuttons or other operator controls 54 may also be included as part of the heater control module for operator-based selection of suitable operating temperature setpoints.

Figure 5A:
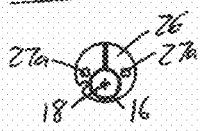
FIGS. 5A through 5F are cross-sectional views of the main body structure of FIGS. 3 and 4, as viewed from lines A-A through F-F thereof, respectively.
Figure 5B:
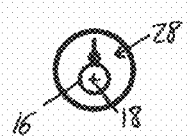
Figure 5C:
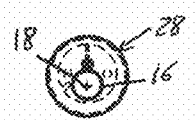
Figure 5D:
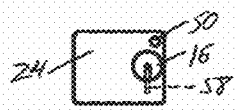
Figure 5E:
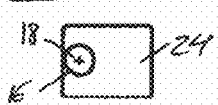
Figure 5F:
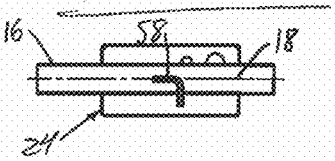

The control unit enclosure 24 also incorporates elements of a forced air system for pressurized conveyance of the vaporized oxalic acid from the apparatus through the diffuser 48 or other final output point at the discharge end 36 of the heatsink chamber body 12. For the such purpose, the illustrated embodiment includes a pneumatic connection fitting 56 mounted to the control unit enclosure 24 to accept connection of an air hose from an external air compressor to provide a pressurized air supply to the apparatus. With reference to FIG. 5F, the forced air system further includes a nozzle 58 that penetrates through the wall of the primary tube 16 from the interior of the control unit enclosure 24, and points axially toward the distal end 22 of the primary tube 16 in order to direct pressurized air received from the connection fitting 56 downstream toward the heatsink chamber body 12.

Figure 10:
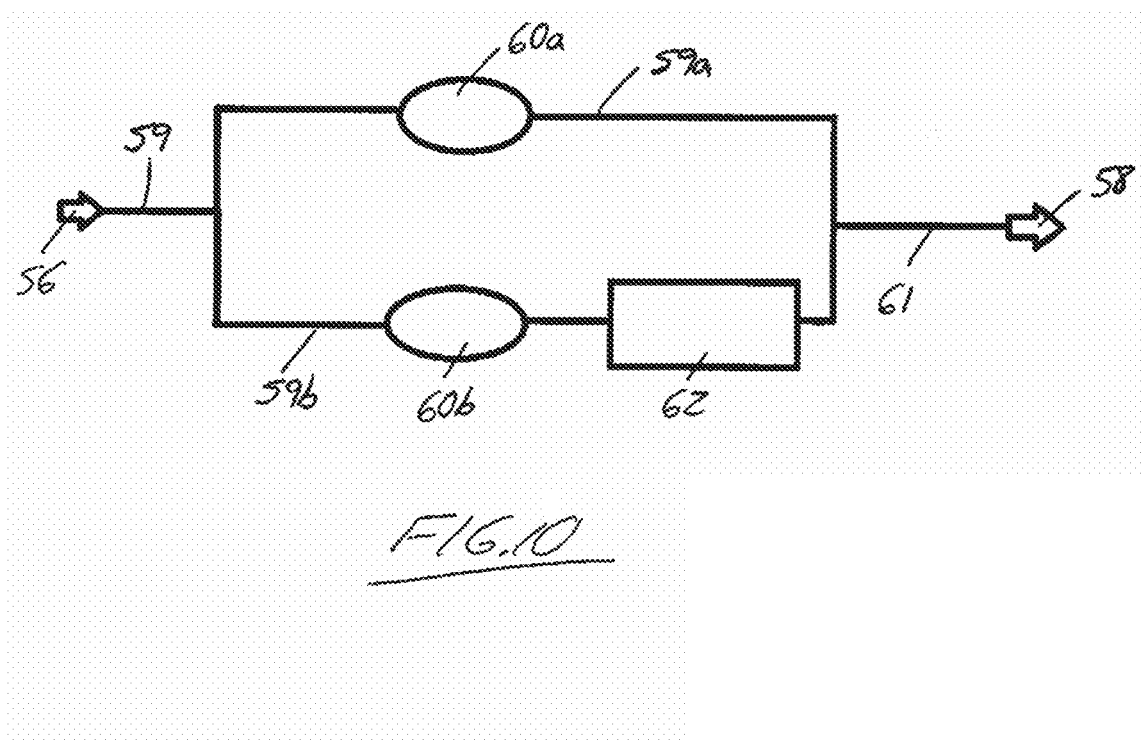
FIG. 10 is a schematic diagram of a forced air system of the apparatus of FIG. 1.

FIG. 10 shows a schematic diagram of the forced air system. An intake airflow path 59 from the connection fitting 56 splits into two parallel branches 59a, 59b each containing a respective flow control valve 60a, 60b for adjusting airflow through the respective branch 59a, 59b. Downstream of these valves 60a, 60b the two branches 59a, 59b join back together to provide a singular path 61 to the nozzle 58 inside the primary tube 16. One branch 59a is always open, and thus serve as a continuous flow branch providing a steady, ongoing stream of pressurized air into the primary tube 16 via the nozzle 58. The other branch 59b is a normally-closed burst-control branch featuring a normally closed on/off valve 62 that is situated downstream of the respective flow control valve 60b. The on/off valve 62 can be temporarily opened by an operator of the apparatus to allow supplementary flow through this second branch 59b in order to augment the continuous airflow through the first branch 59a, thus creating an extra burst of air pressure through the nozzle 58 when the on/off valve 62 is opened.

FIG. 1 shows a pair of valve adjustment actuators in the form of rotatable adjustment knobs 64 disposed atop the control unit enclosure 24 for respective manual adjustment of the flow control valves 60a, 60b. An open-close valve actuator in the form of a thumb lever 66 is also disposed atop the control unit at the end thereof nearest the hand grip portion 16a of the primary tube 16 in order to momentarily open the on/off valve 62 when depressed by the thumb of the operator's hand on this hand grip portion 16a of the primary tube. A power switch connected to the heater control module for activation and deactivation of the heater is also provided, for example in the form of a toggle switch 66 also mounted atop the control unit enclosure.

In use of the apparatus, the operator holds the grip portion 16a of the primary tube 16 in one hand and tips the opposing heater-equipped distal end 22 of the primary tube downward toward ground level to achieve a down-turned orientation of the primary tube 16. Oxalic acid crystals are introduced into the primary tube 16 via the loading port at the open proximal end of the tube 16, and, shown by the solid line arrow in FIG. 11A, the oxalic acid gravitationally falls through the downturned primary tube 16, past the nozzle 58 and onward through the open distal end 22 of the primary tube 16. Since this distal end of the primary tube opens into the vaporization chamber 30 of the heatsink chamber body 12, the crystals fall down into the vaporization chamber 30, past the gap space 43 at the counterbore that opens radially from the vaporization chamber 30 into the exhaust chamber 32. The hollow interior of the primary tube 16 thus defines a delivery passage for routing the oxalic acid crystals into the vaporization chamber from a loading port situated remotely thereof to keep the operators hands far from the high operating temperatures at the vaporization chamber. The delivered crystals settle against the closed end 30a of the vaporization chamber 30. The heat imparted to the heatsink chamber body 12 by the band heater 14 is transferred to the received oxalic acid crystals, causing same to undergo sublimation within the vaporization chamber 30.

Meanwhile, the nozzle 58 of the forced air system provides a steady stream of air through the primary tube 16 into the heatsink chamber body 12. Since the end 30a of the vaporization chamber is closed, the air being pumped into the heatsink chamber body 12 and the vapor resulting from the sublimation of the oxalic acid will exit the heatsink chamber body 12 through the gap space 43 that exits between the two chambers at the counterbored area 38 of the heatsink body's attachment end 34, as shown by the long-dash broken line in FIG. 11A. The pressurized state of the primary tube 16 due to the ongoing stream of air introduced through the nozzle 58 prevents the vaporized oxalic acid from moving upstream into the tube 16. The air stream thus instead forces the vaporized oxalic acid into the lower-pressure environment outside the apparatus via the gap space 43, exhaust channel 32 and outlet diffuser 48, as shown by the short-dash broken line in FIG. 11A.

On an ongoing basis throughout this process, the temperature sensor is actively sampling the temperature of the heatsink chamber body 12 near the vaporization chamber 30, which is in turn read by the heat control module This control module then determines if the temperature is above or below a predetermined or programmable set-point (e.g. a user customized setpoint adjusted via controls 54). If the detected temperature of the heatsink 12 is below the setpoint, the control module activates the heater 14 until the heatsink set-point temperature is reached. A PID controller may be used to reduce overshoot of the setpoint temperature.

The use of a separate heatsink to define the vaporization chamber, rather than using a distally situated portion of the primary tube 16 itself, provides notable advantage in that the heatsink can store a substantial amount of heat energy therein, reducing difficulties in maintaining a relatively constant temperature in the vaporization chamber despite the high amount of heat energy required to vaporize the initially solid substance. The improved heat storage capacity of the heatsink chamber body compared to the primary tube 16 can be attributed to both the dramatically thicker walls surrounding the vaporization chamber versus the much thinner pipe walls of the primary tube 16, and the optional use of more thermally conductive material (e.g. brass, aluminum, etc.) for the heatsink chamber body versus the primary tube 16, whose constituent material(s) (e.g. steel) may be less thermally conductive to reduce risk of burn or discomfort to the user by minimizing heat transfer from the heater-carrying distal end of the primary tube to the hand grip and loading portion 16a of the primary tube at the proximal end.

This solid to vapor state change (sublimation) can thus draw on the stored energy in the heatsink 12 so that the temperature doesn't drop as much during sublimation. This allows continuous use without large delays, as the vaporization chamber can use the stored heat rather than waiting for the heater to catch up with the energy consumption of the sublimation process. Also, since the thermally conductive heatsink provides relatively uniform temperature distribution throughout, accurate sampling of the vaporization chamber temperature can be achieved without having the thermocouple or other sensor in an exposed position in the chamber, where exposure to the acid would be corrosive and detrimental to accurate long-term temperature sampling.

Additionally, by placing the exhaust chamber in radially offset relation to one side of the vaporization chamber, rather than prior art configurations in which the air and vapor flow axially straight through a screened end of vaporization chamber into an inline-exhaust that is merely an axial extension of the same pipe that forms the vaporization chamber, the sold oxalic acid crystals fall directly against a solid, thermally conductive surface at the closed end 30a of the vaporization chamber, thus exposing the crystals to a greater amount of direct, conductive heat transfer than would be provided at a mesh screen surface.

Since various modifications can be made in my invention as herein above described, and many apparently widely different embodiments of same made, it is intended that all matter contained in the accompanying specification shall be interpreted as illustrative only and not in a limiting sense.

The invention claimed is:

1. An apparatus for vaporizing and dispensing a pesticide agent, said apparatus comprising:
    an elongated body structure having a proximal end, an opposing distal end and a delivery passage running longitudinally of the elongated body structure to the distal end thereof;
    a heatsink of thermally conductive material attached to said elongated body structure at the distal end thereof and comprising a hollow interior into which the delivery passage of the elongated body structure opens at the distal end thereof;
    a loading port on the elongated body structure at or proximate the proximal end thereof for introduction of pesticide material into the delivery passage for delivery onward therethrough to the hollow interior of the heatsink;
    a heater operably arranged with the heatsink to vaporize the pesticide material received in the hollow interior of the heatsink through the elongated body structure; and
    a vapour outlet fluidly communicating the hollow interior of the heatsink to an exterior environment to exhaust the vaporized pesticide from the apparatus to a targeted treatment area;
    wherein the heatsink comprises a bored-out solid body of said thermally conductive material.

2. The apparatus of claim 1 wherein the heatsink exceeds the elongated body structure in wall thickness.

3. The apparatus of claim 1 wherein the thermally conductive material of the heatsink is aluminum.

4. The apparatus of claim 1 comprising a temperature sensor operably installed on the heatsink to monitor temperature conditions thereof and connected to a controller arranged to automatically control the heater in response to detected changes in said temperatures conditions.

5. The apparatus of claim 1 wherein the heater is a band heater defining a cylindrical shell around the heatsink.

6. The apparatus of claim 1 wherein the thermally conductive material of the heatsink has greater thermal conductivity than a constituent material of the elongated body structure.

7. An apparatus for vaporizing and dispensing a pesticide agent, said apparatus comprising:
    an elongated body structure having a proximal end, an opposing distal end and a delivery passage running longitudinally of the elongated body structure to the distal end thereof;
    a heatsink of thermally conductive material attached to said elongated body structure at the distal end thereof and comprising a hollow interior into which the delivery passage of the elongated body structure opens at the distal end thereof;
    a loading port on the elongated body structure at or proximate the proximal end thereof for introduction of pesticide material into the delivery passage for delivery onward therethrough to the hollow interior of the heatsink;
    a heater operably arranged with the heatsink to vaporize the pesticide material received in the hollow interior of the heatsink through the elongated body structure; and
    a vapour outlet fluidly communicating the hollow interior of the heatsink to an exterior environment to exhaust the vaporized pesticide from the apparatus to a targeted treatment area;
    wherein the thermally conductive material of the heatsink has greater thermal conductivity than a constituent material of the elongated body structure.

8. The apparatus of claim 7 wherein the heatsink comprises a bored-out solid body of said thermally conductive material.

9. The apparatus of claim 7 wherein the heatsink exceeds the elongated body structure in wall thickness.

10. The apparatus of claim 7 wherein the thermally conductive material of the heatsink is aluminum.

11. The apparatus of claim 7 wherein the heater is a band heater defining a cylindrical shell around the heatsink.

12. An apparatus for vaporizing and dispensing a pesticide agent, said apparatus comprising:
    an elongated body structure having a proximal end, an opposing distal end and a delivery passage running longitudinally of the elongated body structure to the distal end thereof;
    a heatsink of thermally conductive material attached to said elongated body structure at the distal end thereof and comprising a hollow interior into which the delivery passage of the elongated body structure opens at the distal end thereof;
    a loading port on the elongated body structure at or proximate the proximal end thereof for introduction of pesticide material into the delivery passage for delivery onward therethrough to the hollow interior of the heatsink;
    a heater operably arranged with the heatsink to vaporize the pesticide material received in the hollow interior of the heatsink through the elongated body structure; and
    a vapour outlet fluidly communicating the hollow interior of the heatsink to an exterior environment to exhaust the vaporized pesticide from the apparatus to a targeted treatment area;
    wherein the heater is a band heater defining a cylindrical shell around the heatsink.

13. An apparatus for vaporizing and dispensing a pesticide agent, said apparatus comprising:
  an elongated body structure having a proximal end, an opposing distal end spaced therefrom in an axial direction and a delivery passage running longitudinally of the elongated body structure to the distal end thereof;
  a vaporization chamber carried at the distal end of the elongated body structure, where the delivery passage of the elongated body structure opens into said vaporization chamber;
  a loading port on the elongated body structure at or proximate the proximal end thereof for introduction of pesticide material into the delivery passage for delivery onward therethrough to the vaporization chamber;
  a heater operably arranged with the vaporization chamber to vaporize the pesticide material received therein through the delivery passage to generate a pesticidal vapour; and
  an exhaust chamber for receiving the pesticidal vapour from the vaporization chamber; and
  a vapour outlet fed by the exhaust chamber to exhaust the pesticidal vapour from the apparatus to a targeted treatment area;
  wherein the vaporization chamber has a first open end into which the delivery passage opens and a closed second end axially opposite the first open end, and the exhaust chamber is radially offset from the vaporization chamber and is fluidly communicated therewith near the first end thereof.

14. The apparatus of claim 13 wherein the exhaust chamber communicates with the vaporization chamber and the vapor outlet adjacent axially opposing ends of said exhaust chamber.

15. The apparatus of claim 13 wherein the chambers are in fluid communication with one another only at areas thereof adjacent the distal end of the elongated body structure.

16. The apparatus of claim 13 wherein the chambers comprise respective cylindrical bores in a shared body of material.

17. The apparatus of claim 16 wherein the respective cylindrical bores of the chambers are fluidly communicated with one another at a counter-bored end of the shared body of material.

18. The apparatus of claim 13 wherein the heater is disposed circumferentially around both the vaporization chamber and the exhaust chamber.

19. The apparatus of claim 13 wherein the heater is a band heater defining a cylindrical shell around the vaporization chamber.

20. The apparatus of claim 13 comprising a forced air system for pressurized conveyance of the pesticidal vapour from the vaporization chamber to the vapour outlet via the exhaust chamber, said forced air system comprising a nozzle arranged to introduce a supply of pressurized air into the delivery passage and direct said supply of pressurized air through said delivery passage to the vaporization chamber.

21. The apparatus of claim 20 wherein said nozzle is an only nozzle of said forced air system, which further comprises two different supply branches that both feed said only nozzle, one of said branches comprising a burst control valve operable from a normally closed state to an open state to momentarily open said one said branches to augment a steady supply of air through the other branch with a momentary burst of additional air.

* * * * *